US00PP37281P3

(12) United States Plant Patent
Bloodworth

(10) Patent No.: US PP37,281 P3
(45) Date of Patent: Feb. 24, 2026

(54) GRAPEVINE PLANT NAMED 'JB 12-24-E4-12'

(50) Latin Name: **Intersubgeneric hybrid of *Muscadinia Planch.* and *Euvitis* Planch. of the genus *Vitis***
Varietal Denomination: JB 12-24-E4-12

(71) Applicant: Early Morning LLC, Greendale, IN (US)

(72) Inventor: Patterson Jeffrey Bloodworth, Hillsborough, NC (US)

(73) Assignee: EARLY MORNING LLC, Greendale, IN (US)

( * ) Notice: Subject to any disclaimer, the term of this patent is extended or adjusted under 35 U.S.C. 154(b) by 123 days.

(21) Appl. No.: 18/489,982

(22) Filed: Oct. 19, 2023

(65) Prior Publication Data

US 2025/0127135 A1 Apr. 24, 2025

(51) Int. Cl.
*A01H 5/08* (2018.01)
*A01H 6/88* (2018.01)

(52) U.S. Cl.
USPC ..... Plt./207
CPC ..... *A01H 6/88* (2018.05); *A01H 5/08* (2013.01)

(58) Field of Classification Search
USPC ..... Plt./207, 205
CPC ..... A01H 5/08; A01H 5/00; A01H 6/88
See application file for complete search history.

*Primary Examiner* — June Hwu
(74) *Attorney, Agent, or Firm* — Weatherly IP Solutions, LLC; James M. Weatherly

(57) ABSTRACT

A new grapevine plant particularly distinguished by large, seedless, attractively colored berries borne in well-filled clusters, unlike traditional seeded muscadines, which are marketed as individual berries, typical muscadine aroma and flavor, is disclosed.

3 Drawing Sheets

Genus and species: Intersubgeneric hybrid of *Muscadinia* Planch. and *Euvitis* Planch. of the genus *Vitis*.
Variety denomination: 'JB 12-24-E4-12'.

BACKGROUND OF THE NEW PLANT

The present invention relates to a new and distinct variety of grapevine hereinafter referred to by the variety name 'JB 12-24-E4-12'.

'JB 12-24-E4-12' arose from a controlled cross in 2012 in Hillsborough, North Carolina between a proprietary and unpatented grapevine named 'JB 99-1-4-15' (the results of a cross between Supreme and an Open Pollination) female parent, and a proprietary and unpatented grapevine named 'JB 06-23-1-4' (Ga 9-11-2 x JB 03-20-1-21). Seeds and seedlings from the cross were sown and planted in Wasco, CA in 2013 and 'JB 12-24-E4-12' was selected in September 2015.

'JB 12-24-E4-12' was first asexually propagated in 2015 in Wasco, CA by softwood cuttings. 'JB 12-24-E4-12' was found to reproduce true to type in successive generations of asexual propagation via softwood cuttings.

SUMMARY

The following are the most outstanding and distinguishing characteristics of this new variety when grown under normal horticultural practices in Hillsborough, North Carolina.

1. Large, seedless, attractively colored berries borne in well-filled clusters, unlike traditional seeded muscadines, which are marketed as individual berries.

2. Typical muscadine aroma and flavor combined with relatively thin, more edible skin and juicier flesh compared to most traditional seeded muscadine cultivars.

DESCRIPTION OF THE PHOTOGRAPHS

This new grapevine plant is illustrated by the accompanying photographs which shows the plant's overall plant habit. The colors shown are as true as can be reasonably obtained by conventional photographic procedures.

DESCRIPTION OF THE NEW VARIETY

Figure 1:
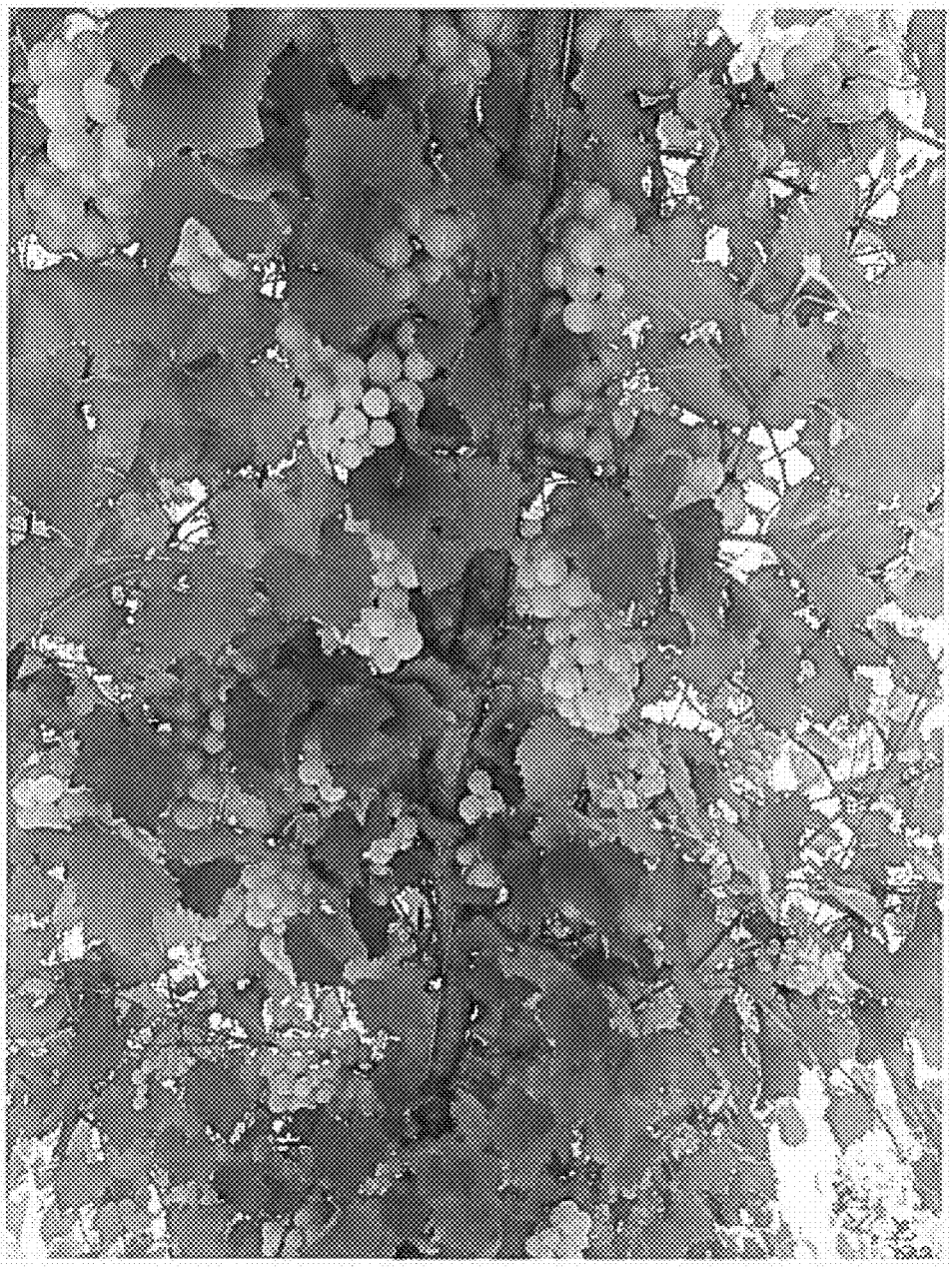
FIG. 1 shows the overall plant, leaves and fruit of 'JB 12-24-E4-12' at five years old, taken in Hillsborough, North Carolina in September of 2021.
Figure 2:
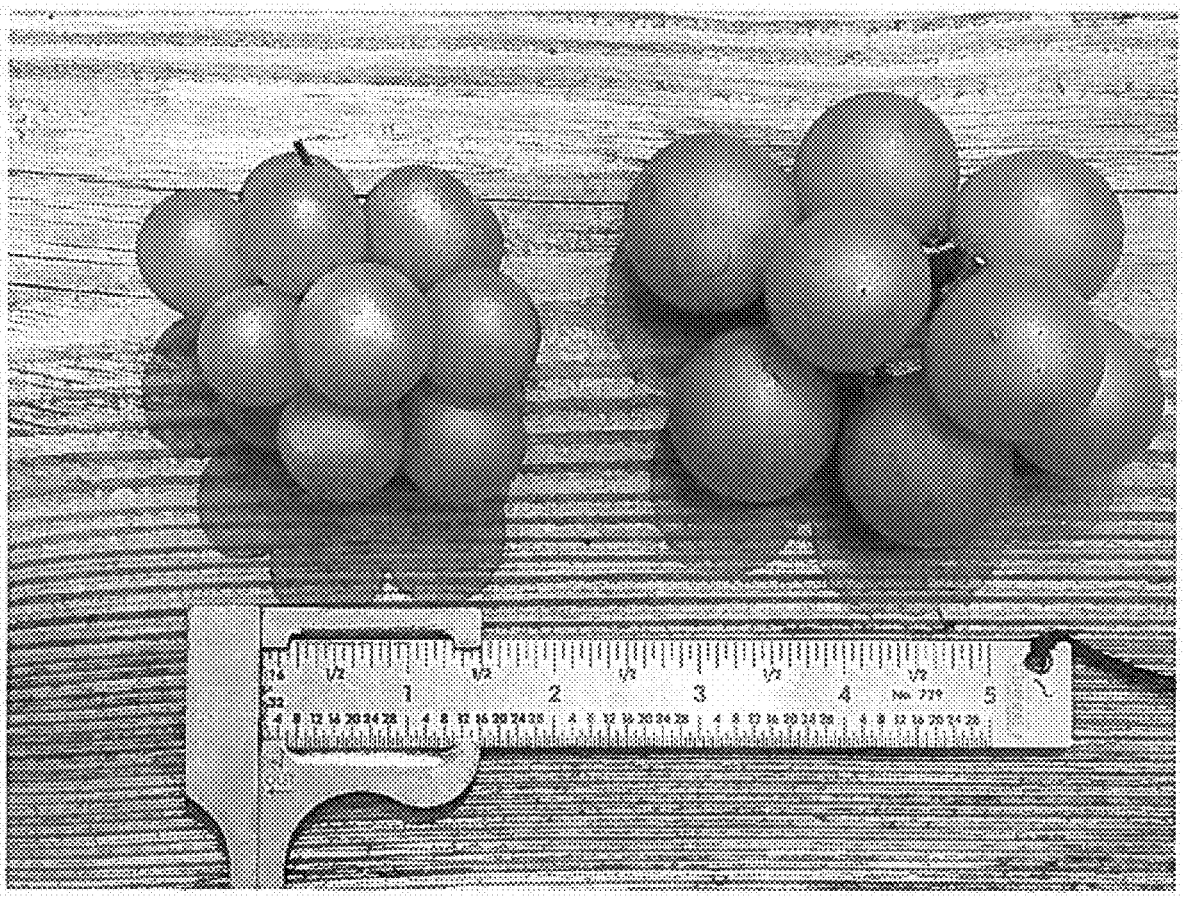
FIG. 2 shows a cluster of 'JB 12-24-E4-12' (left) in comparison to the seeded commercial variety 'Fry'.
Figure 3:
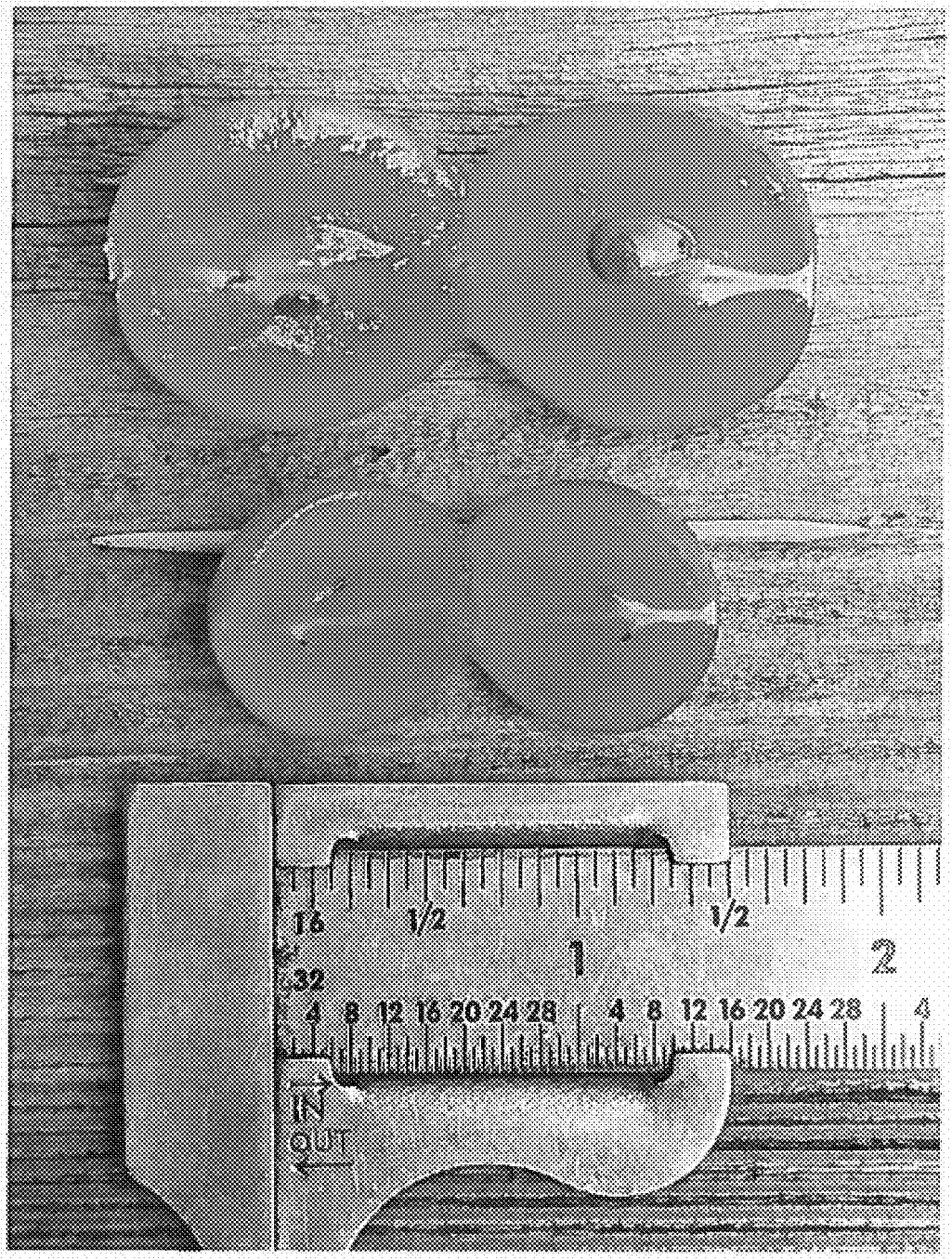
FIG. 3 shows the sectioned fruit of stenospermocarpic seedless 'JB 12-24-E4-12' (below) in comparison to that of the seeded commercial variety 'Fry'.

The following detailed descriptions set for the distinctive characteristics of 'JB 12-24-E4-12'. Measurements were taken from two own-rooted vines, aged seven and four years old, observed in the field and under artificial daylight halogen illumination in Hillsborough, North Carolina from April to September 2023. Color references are to The R.H.S. Colour Chart of The Royal Horticultural Society of London (R.H.S.) 2007, Fifth Edition.

Classification:

*Family*.—Vitaceae.

*Botanical*.—Hybrid between subgenus *Muscadinia* Planch. (primarily *Vitis rotundifolia*) and subgenus

*Euvitis* Planch. (primarily *Vitis vinifera*, the donor of perfect-floweredness and stenospermocarpic seedlessness).

*Designation*.—'JB 12-24-E4-12'.

Plant:

*Plant habit and growth*.—Recumbent, climbing.

*Size*.—Large.

*Height*.—6'.

*Width*.—4'.

*Age at maturity*.—3 years.

*Vigor*.—High.

*Productivity*.—High to the point of overproduction if not properly, severely pruned.

*Cold hardiness/winter hardiness/temperature tolerance*.—One vine, planted in 2016, suffered no apparent winter cold injury after a low temperature of −2° F. in January 2019.

Trunk:

*Diameter*.—2.5 inches measured at 2.0 feet above ground (2016 planting).

*Surface texture*.—Rough.

*Color*.—RHS 200C to 200D (old bark), RHS 177B to 177C (freshly exposed).

Canes:

*Diameter*.—Immature: 4-5/32"×5/32". Mature: 3/8"×5/16", 3rd proximal internode.

*Length*.—Up to 9.5 feet.

*Surface texture*.—Immature cane: Smooth, barely visible lenticels appear at the 12th internode from shoot tip. Mature cane: Rough with numerous raised lenticels. Form (woody cross-section form): Elliptical.

*Color*.—Immature: RHS 146A, 12th internode from apex, no anthocyanin. Mature: RHS 177B.

*Internode length* (*upper mature sun cane*).—2" to 3".

*Internode color*.—RHS144A (green) with anthocyanin absent.

*Time of bud burst*.—April 8, swollen buds, April 14, green tissue visible, April 15, fully burst.

Tendrils:

*Form*.—Unbranched.

*Size*.—Length: Up to 5". Diameter: 1/32".

*Texture and distribution*.—Smooth, at node opposite petiole, absent at every third node.

*Color*.—Immature: RHS 144A, 1.5" in length. Anthocyanin: No. Mature: RHS 152A before becoming woody. Anthocyanin: No.

Growing tips (young shoots):

*Pubescence*.—Present.

*Color*.—RHS 144A.

*Anthocyanin*.—Absent.

*Shape*.—Shepherd's Crook.

*Apex*.—Exposed or fully open.

*Pubescence*.—Present, prostrate hairs on third to distal internode medium in density.

Leaves:

*Shape*.—Orbicular.

*Apex*.—Pointed.

*Base*.—Sagittate.

*Margin*.—Dentate.

*Length of teeth on margin*.—1/8" to 3/8".

*Shape of teeth on margin*.—Dentate, straight to slightly convex.

*Number of leaf lobes on mature leaf*.—Indistinctly 5-lobed.

*Texture*.—Immature: Upper surface: Smooth. Lower surface: Slightly rough with raised veins. Mature: Upper surface: Smooth. Lower surfaces: Slightly rough with raised veins.

*Size*.—Immature leaf: Length: 2.5". Width: 2.75". Mature leaf: Length: 3.25". Width: 4.25".

*Color*.—Immature leaf: Upper surface: RHS 144A. Lower surface: RHS 144A. Mature: Upper surface: RHS 137A. Lower surface: RHS 137B.

*Venation*.—Pattern: Palmate. Color: Upper surface: RHS 146A. Lower surface: RHS 146B.

*Pubescence*.—Prostrate Hairs Between Main Veins on Lower Leaf Surface. Immature: medium to sparse density on leaf measuring 7/16 inch wide. Mature: very sparse density. Erect hairs on Main Veins of Lower Mature Leaf: very sparse only near vein junctions.

Petiolar sinus: Open, lyre shaped.

Petiole:

*Length*.—2.75" to 3.25".

*Diameter*.—1/16".

*Color*.—RHS 152A (Ribs) RHS 144B (Grooves).

Floral cluster:

*General description and location*.—Panicle, at node opposite leaf.

*Quantity of florets per cluster*.—79.

*Length*.—1 5/8".

*Width*.—1.5".

*Peduncle length*.—3/8"-1 5/8".

Inflorescences: Perfect-Flowered.

*Quantity of inflorescences per shoot*.—2-3.

*Pistil*.—Length: 3/32". Diameter: 1-5/32". Color: RHS 152B.

*Filament*.—Length: 2-5/32". Color: RHS 193B.

*Anther*.—Shape: Oblong, Ovate. Color: RHS 18C.

*Stamen*.—Form: Upright. Quantity: 6 to 7/floret. Length: 3/32". Color: Not Applicable.

*Date of bloom*.—June 9 to June 15.

*Pollen amount*.—Abundant.

*Calyptra*.—Sheds normally.

*Calyptra color*.—RHS 144C.

Plant:

*Plant habit and growth*.—Recumbent, climbing.

*Size*.—Large.

Fruit:

*Time of year of commercial harvest & shipment*.—First ripe September 7, Main crop September 11 to October 7, small to medium secondary crop on lateral shoots.

*Cluster*.—General Type: Panicle. Size: Medium to large for *V. rotundifolia*, small for *V. vinifera*. Length, without peduncle: 2.5" to 3". Width: 2.5" to 3.5". Density: Well-filled. Shape and weight of cluster: Globular, 1.9 to 3.7 oz.

*Peduncle*.—Length: Variable, Range: 3/8" to 1 5/8". Mean is 0.87". More vigorous shoots have longer peduncles. Severe pruning to prevent overcropping should result in higher shoot vigor and provide longer peduncles, facilitating cluster harvest. Peduncles shorter than about 7/8" make cluster harvest more difficult. Diameter: 1/16". Color: RHS N199B. Number of berries per cluster: Up to 21.

*Berry*.—Size: Medium to large. Shape: Spherical. Uniformity: Acceptable. Length: Mean is 13/16", Max is 15/16". Width/Diameter: Mean is 13/16", Max is 15/16".

Skin. Type: Slip Skin. Skin color: RHS 153D, near ripe; RHS 164B, fully ripe. Lenticels: Medium to high in density, size minute up to 0.023" in diameter, color RHS 165A. Thickness: 1/16" as manually peeled from flesh. Texture: crunchy, relatively tender, fragments easily, non-astringent. Waxy Bloom: None. Weight of individual berry: Mean is 4.57 gm on slightly overcropped vines. Maximum is 6.5 gm.

*Pedicel*.—Length: 5/32". Diameter: 1/16". Color: RHS 199B. Strength of attachment to berry: Strong, detaches with wet scar, rarely with a broken pedicel attached to the berry, A small percentage will shell in handling and storage.

*Flesh*.—Color: RHS 150D, translucent. Juice color: RHS 155D, clear. Juice production: high. Texture: Mucilaginous, almost totally melting. Brix: Mean when ripe: 18.6°, Individual berries: up to 20.2°. Flavor: Fruity, musky. Fragrance: Flowery, fruity, musky. Fresh fruit can be marketed in bags or baskets and can be held in clamshells for 2-3 weeks at 33 degrees F. In high humidity.

Seed traces:

*Length*.—Minute up to 3/32".

*Width*.—Minute up to 1/32".

*Texture*.—Soft.

*Perception*.—Unnoticeable.

Disease and insect resistance: Both parents of 'JB 12-24-E4-12' are resistant to the common muscadine berry rots. 'JB 12-24-E4-12' has minimum berry rot incidence under a standard pesticide spray program including fungicides: Manzate Pro-Stick, Nova, and Captan.

Cultural note: Ripe berries of 'JB 12-24-E4-12' appear largely resistant to skin cracking induced by significant rainfall, with only minimal incidence of cracking observed.

COMPARISON WITH PARENTAL LINES AND KNOWN VARIETY

'JB 12-24-E4-12' is a distinct variety of Grapevine and is distinguished from its parents as described in Table 1 and Table 2:

TABLE 1

Comparison with Female Parental Line

| Trait | Variety 'JB 12-24-E4-12' | Female parent 'JB99-1-4-15' |
|---|---|---|
| Seed | Seedless | Seeded |
| Sex | Perfect-flowered | Female |

TABLE 2

Comparison with Male Parental Line

| Trait | Variety 'JB 12-24-E4-12' | Male Parent 'JB06-23-1-4' |
|---|---|---|
| Fruit size | Larger than male parent | Smaller than 'JB 12-24-E4-12' |

'JB 12-24-E4-12' is most similar to the commercial grapevine variety 'Tara' (unpatented). Differences between the varieties are described in Table 3.

TABLE 3

Comparison with Commercial Line

| Characteristic | 'JB 12-24-E4-12' | Commercial line 'Tara' |
|---|---|---|
| Seed | Seedless | Seeded |

I claim:

1. A new and distinct cultivar of grapevine plant named 'JB 12-24-E4-12' as illustrated and described herein.

* * * * *